United States Patent [19]

Brinkhoff et al.

[11] Patent Number: 4,536,892
[45] Date of Patent: Aug. 27, 1985

[54] RIOT FACESHIELD ASSEMBLY

[75] Inventors: Carl H. Brinkhoff, Pittsburgh; Gordon C. Scott, Verona, both of Pa.

[73] Assignee: Mine Safety Appliances Company, Pittsburgh, Pa.

[21] Appl. No.: 602,850

[22] Filed: Apr. 23, 1984

[51] Int. Cl.³ .............................................. A61F 9/04
[52] U.S. Cl. ............................................. 2/424; 2/10
[58] Field of Search ...................... 2/424, 10, 6, 8, 9, 2/185 R, 199, 422, 13

[56] References Cited

U.S. PATENT DOCUMENTS 3,214,768 11/1965 Bohner .................................... 2/10
3,553,734 1/1971 Aileo ...................................... 2/10

FOREIGN PATENT DOCUMENTS 2061696 5/1981 United Kingdom ................... 2/424

Primary Examiner—Werner H. Schroeder
Assistant Examiner—J. L. Kravitz
Attorney, Agent, or Firm—Reed, Smith, Shaw & McClay

[57] ABSTRACT

A riot faceshield assembly is provided which can be utilized with a wide range of protective helmet designs and sizes, which provides a positive sealing relationship between the faceshield and the front brim of the helmet, which may be pivoted into and conveniently locked in the protective position, and which includes a positive stop member to prevent the faceshield from pivoting downwardly into contact with a wearer's neck or chest when impacted. The faceshield assembly includes a three point or triangular retention system which assures integrity of the unit in the event of either upwardly or downwardly directed impacts.

8 Claims, 8 Drawing Figures

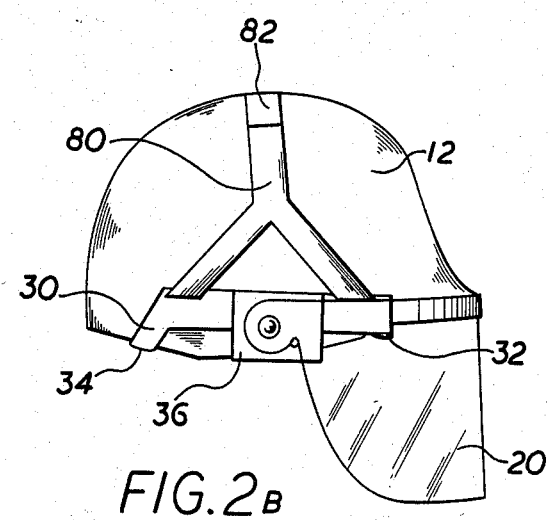
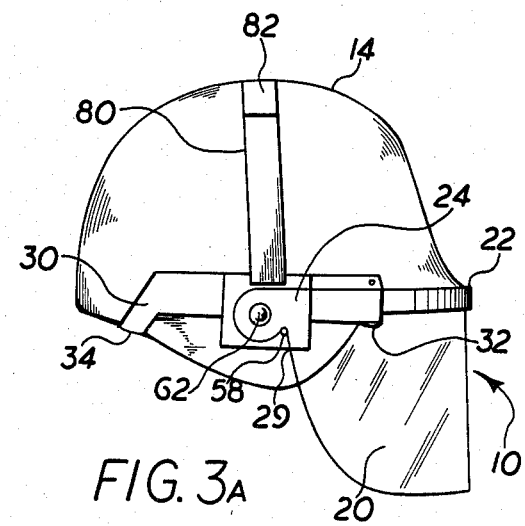
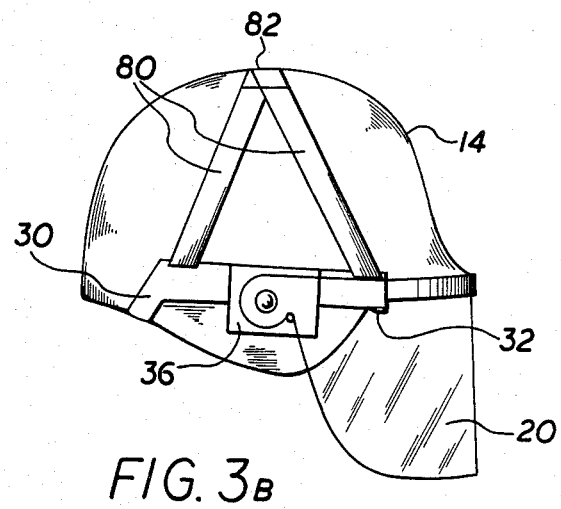

RIOT FACESHIELD ASSEMBLY

FIELD OF THE INVENTION

The invention relates to riot faceshield assemblies adapted for use in connection with protective riot helmets, and more particularly to faceshield assemblies which are securely attachable to and detachable from helmets not specially equipped for such devices.

DISCUSSION OF THE TECHNICAL PROBLEM

Various configurations of protective faceshields for use with protective helmets have been employed, some of which are attachable to helmets not particularly equipped for such attachment, or even directly to a person's head. An example of such a device is found in U.S. Pat. No. 3,214,768 to Bohner, in which a protective faceshield (or welder's shield) is pivotably fastened to a helmet or head through the use of a headband which extends about the head from forehead to rear. The headband is adjustable at the rear for use with helmets or heads of differing sizes, and is assisted in its function by a crown strap which extends at right angles to the headband over the crown of the head. While useful as a welder's shield or in a similar environment, such a device would be seriously limited if used as a riot faceshield because it could be easily jarred from the helmet or head of the wearer, and because it fails to provide a seal between the helmet brim and the faceshield to protect the eyes and face of the wearer from dangerous objects or liquids approaching from above.

Another device more suitable for use as a riot faceshield has been employed by the U.S. military with the conventional metal M1 helmet, and includes an elongated channel which is shaped to correspond to and fit along the front brim of the helmet. An elongated spring extends around the back of the helmet similar to the headband of the Bohner patent, and a hook in the center thereof secures to a lip on the rear brim to maintain the elongated spring in the desired position. This device is more suitable for riot use because of its more secure retention to the helmet and because it provides an acceptable seal between the front brim of the helmet and the faceshield.

However, this faceshield assembly is limited because a sharp upwardly directed blow from the rear could potentially release the spring and dislodge the faceshield from the helmet. Also lacking is a facility to conveniently lock the faceshield in its down position. Finally, with the introduction by the military of its Personal Armor System Ground Troop (PASGT) helmet in a variety of different sizes and without the rear lip on its brim, the desirability of the above-described faceshield assembly has been diminished, because a different dimension of faceshield assembly is effectively required for each helmet size in order to achieve the desired seal between the front brim of the helmet and the faceshield, and because the elongated spring can readily slip off the rear of the helmet and injure or inconvenience the wearer.

Accordingly, it would be desirable to have a faceshield assembly for riot use which would be universally adaptable for any size of military helmet; which would provide a proper seal between the front brim of the helmet and the faceshield; which would be securely fastened to the helmet to remain in position in the face of both upwardly or downwardly directed impacts; which would permit the faceshield to be conveniently locked in its down, protective position; and which would provide a positive limit to the downward pivotal movement of the faceshield to further protect the wearer.

SUMMARY OF THE INVENTION

The present invention provides a faceshield assembly suitable for riot use which is universally applicable to a wide range of protective helmet designs and sizes and which provides a proper sealing relationship between faceshield and helmet for such wide range of helmets. The faceshield assembly of the present invention is securely retained to such helmets by an opposed, three-point retention system in a manner to remain in position in the event of upwardly or downwardly directed impacts. Additionally, facilities are provided to limit the downward pivotal movement of the faceshield to protect the wearer; to lock the faceshield in the protective position; and to prevent loosening of the faceshield through repeated pivotings thereof.

The faceshield assembly includes a transparent faceshield, first and second bracket members, each including front and rear helmet engaging arms and an intermediate faceshield fastening portion to which the faceshield is pivotally secured. A crown strap attaches to the bracket members and extends over the crown of the helmet. A resilient sealing member engages the front edge of the helmet and facilities are provided to adjust the position of the faceshield relative to the helmet to assure a proper sealing relationship between sealing member and helmet.

BRIEF DESCRIPTION OF THE DRAWINGS

FIGS. 2A and 2B are side views of the faceshield assembly of FIG. 1 in position on a military M1 helmet.

FIGS. 3A and 3B are side views of the faceshield assembly of FIG. 1 in position on a military PASGT helmet.

DESCRIPTION OF THE PREFERRED EMBODIMENTS

Figure 1:
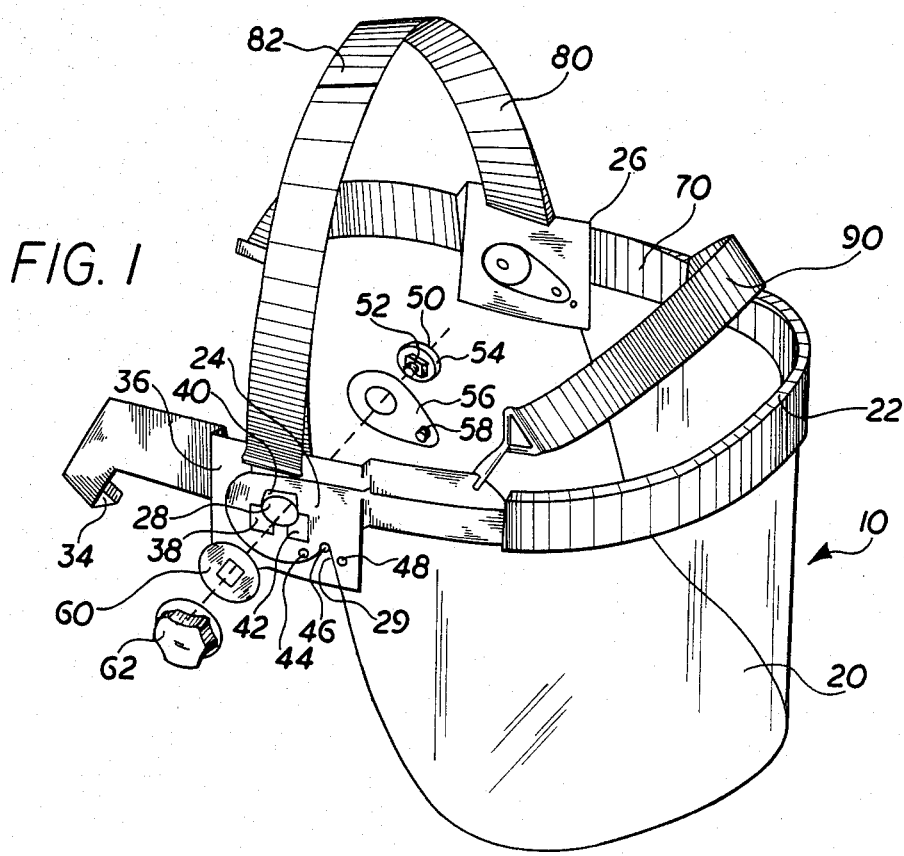
FIG. 1 is a perspective view of the faceshield assembly according to the present invention, with certain elements in exploded view for purposes of clarity.
Figure 2A:
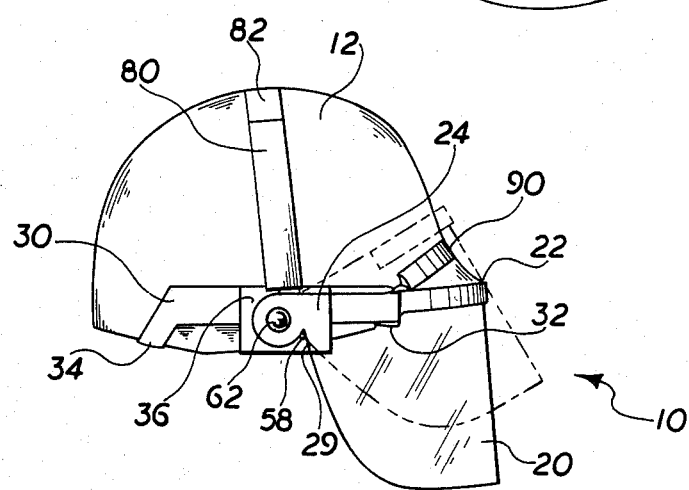

With reference to FIG. 1, a riot faceshield assembly 10 according to the present invention is shown, including as major elements a transparent faceshield 20, a right side bracket member 30, a left side bracket member 70, and a crown strap 80. As shown in FIGS. 2 and 3, the faceshield assembly 10 is designed for universal use with a wide variety of different shaped helmets, e.g., military M1 helmet 12 of FIGS. 2A and 2B or PASGT helmet 14 of FIGS. 3A and 3B. In addition, as discussed more fully below, the invention is designed to be used with a wide range of different helmet sizes while retaining its advantageous characteristics of providing a positive seal between helmet and faceshield 20 adjacent a wearer's eyes, limiting downward pivotal movement of faceshield 20 to protect the wearer from injury, assuring retention of faceshield 20 on the helmet when impacted from any direction and providing a convenient facility for locking faceshield 20 in its protective orientation.

Figure 4:
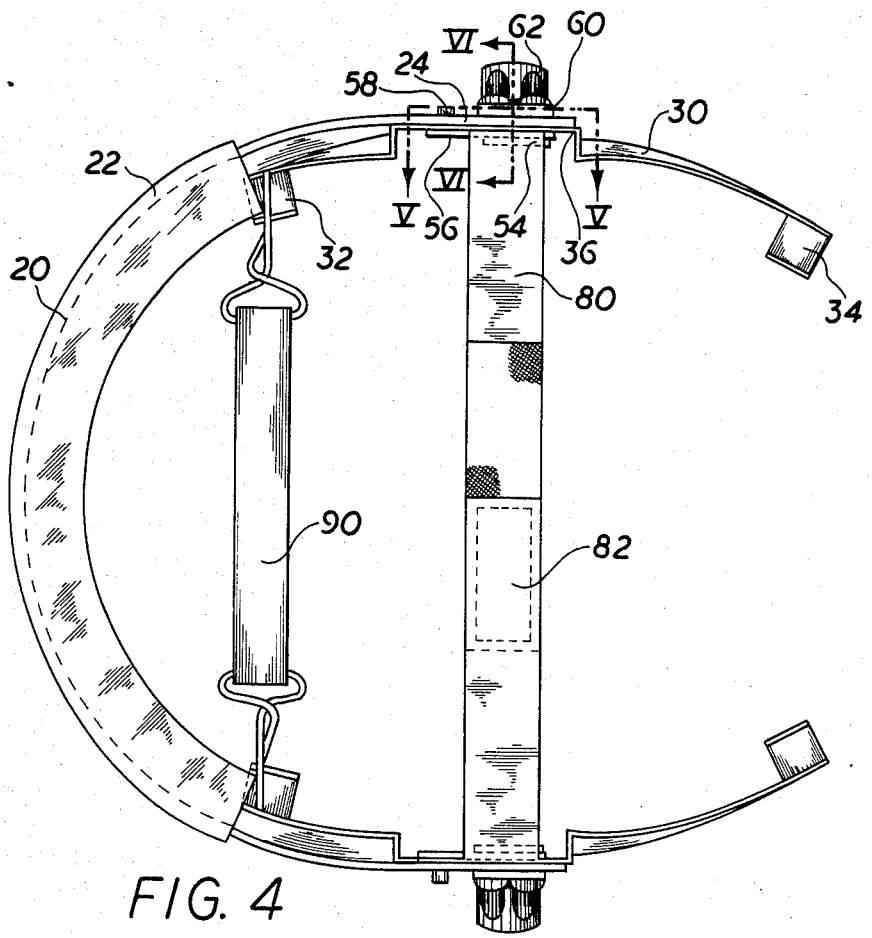
FIG. 4 is a plan view of the faceshield assembly according to the present invention.

With reference also to FIG. 4, the particular configuration of faceshield 20 is not limiting to the invention and may be of any convenient and protective shape and size, although preferably the shape is adapted to permit convenient pivotal movement thereof from a down and protective orientation to an up and out of service position (see FIG. 2). Faceshield 20 is preferably formed of a transparent material which can withstand considerable impact without damage and regular cleanings without undesirable scratching, e.g., polycarbonate. Materials of this type are known in the art and need not be further discussed herein.

Preferably faceshield 20 also includes a resilient sealing member 22 along its upper front edge to facilitate the creation of a sealing relationship between faceshield 20 and helmet 12 or 14 in the area adjacent the wearer's eyes. Such a seal can be very important in riot conditions where chemicals, dangerous liquids and flying articles and debris can incapacitate the wearer if allowed to infiltrate directly into the eyes of the wearer.

Figure 5:
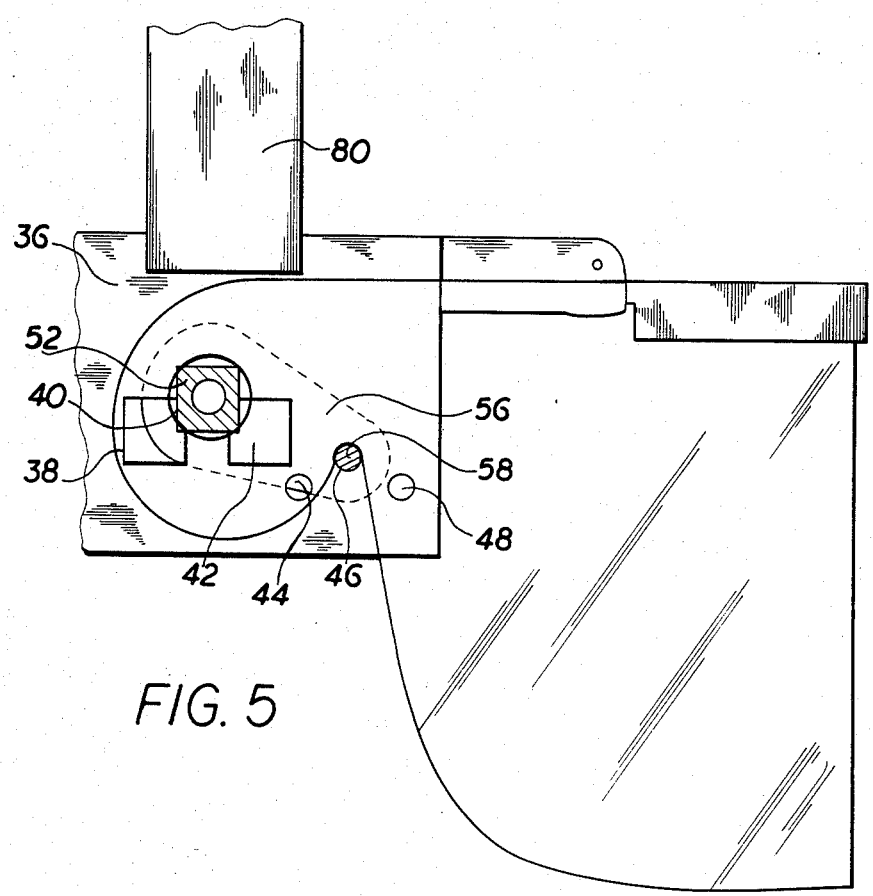
FIG. 5 is a view taken along line 5—5 of FIG. 4.

As best shown in FIGS. 1 and 5, faceshield 20 also includes opposed extending portions 24 and 26 which are pivotally secured to bracket members 30 and 70, respectively, through mounting orifices 28 in a manner discussed below.

Brackets 30 and 70 are preferably complimentarily shaped, such that a detailed description of bracket 30 should suffice herein. Bracket 30 is an elongated substantially rigid, curved member which extends generally along the lower side edge of the helmet, and includes a front edge-engaging arm 32, a rear edge-engaging arm 34 and an intermediate faceshield fastening portion 36 therebetween. As best shown in FIGS. 1-4, edge engaging arms 32 and 34 may be formed in U-shaped configurations to conveniently engage the lower edge of the helmet near front and rear, respectively, to keep faceshield assembly 10 from moving upwardly in response to any impact thereon. Although not limiting to the invention, the angular orientation of engaging arms 32 and 34 may be adapted for a particular helmet, e.g., rear engaging arm 34 might be angled differently in FIG. 2 than in FIG. 3 to correspond to the differing slopes of the rear edges of the helmets shown therein. As best seen in FIG. 3, front engaging arm 32 is preferably oriented to rest at a position along the edge of the helmet where the contour thereof changes, e.g., at the bend in the helmet edge near the front of the earcovering portion. In this manner, the shape of the helmet edge resists any rearward movement of front engaging arm 32 therealong, in the event of a rearwardly directed impact.

Acting in substantial opposition to engaging arms 32 and 34 is crown strap 80, which is secured in any convenient manner to bracket 30, e.g., at a point intermediate engaging arms 32 and 34. Crown strap 80 is preferably formed of a non-stretchable flexible material, and includes length-adjusting means 82 at some point along its length. Alternatively, crown strap 80 may consist of more than a single length and may fasten to bracket 30 with one extension thereof adjacent arm 32 and one extension thereof adjacent arm 34, in the form of an inverted Y as shown in FIG. 2B or in the form of an inverted V as shown in 3B.

In each of the embodiments, an as best shown in FIGS. 2A and 2B and 3A and 3B, crown strap 80 may be oriented over the crown of the helmet and is tightened thereon by adjusting means 82 to exert an upward bias upon brackets 30 and 70 to retain engaging arms 32 and 34 firmly against the lower edge of the helmet. In this manner, each side of faceshield assembly 10 is firmly secured to the helmet with a three-point or triangular series of opposing forces which assures stability whether impact is upwardly or downwardly directed.

In a preferred embodiment of the invention, length-adjusting means 82 comprises a hook and loop mechanism of the type known in the fastening arts under the tradename "Velcro" and available from Velcro Corp. of New York, N.Y. However, in the interest of faceshield security in riot conditions, the fastening strip used in the present invention preferably does not include the non-secured tab portion often provided in such systems to facilitate detachment. Of course length-adjusting means 82 could also be formed of other fastening means such as clamps, buckles, etc., without departing from the intent of the present invention. It will be appreciated that the ready adjustability of crown strap 80 permits faceshield assembly 10 to be conveniently used with a large variety of helmets, differing both in configuration and in size.

Figure 6:
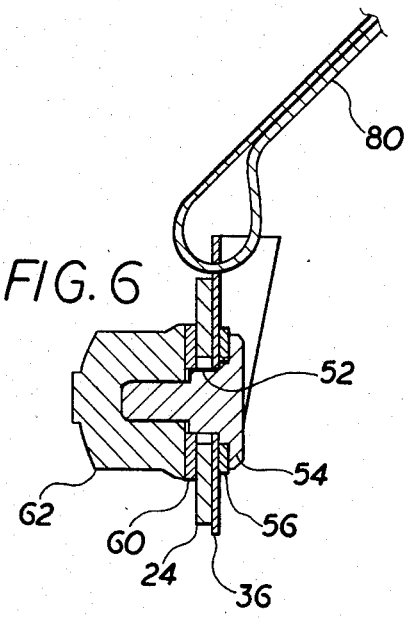
FIG. 6 is a view taken along line 6—6 of FIG. 4.

With continued reference to FIGS. 1 and 4, and with reference also now to FIGS. 5 and 6, faceshield fastening portion 36 of bracket 30 is located relative to the helmet so that the front edge or brim of the helmet aligns vertically with sealing member 22 on faceshield 20 when faceshield 20 is pivoted into its downward or protective orientation. Additionally, to facilitate pivoting of faceshield 20, fastening portion 36 may conveniently be extended slightly outward from the arc connecting engaging arms 32 and 34, and should be substantially vertical in orientation.

Three preferably square or rectangular shaped holes 38, 40, and 42 are disposed in faceshield fastening portion 36, each being a different distance from the front edge thereof. Three smaller circular holes 44, 46, and 48 are disposed in fastening portion 36 in position to correspond to holes 38, 40, and 42, respectively. A threaded bolt member 50 having a squared shoulder portion 52 adjacent its head 54 is inserted through a first washer member 56, through a selected one of holes 38, 40 or 42, through mounting orifice 28 of faceshield 20, through a second washer member 60 having a squared orifice corresponding to squared shoulder portion 52 of bolt 50, and is threadingly engaged to enlarged nut 62. As nut 62 is tightened to bolt member 50, an extending pin 58 on the outwardly facing surface of first washer member 56 is aligned and inserted through the appropriate one of holes 44, 46 or 48 to lock first washer member 56 into nonrotating position relative to fastening portion 36. Likewise, the interfitting of shoulder portion 52 in one of squared holes 38-42 locks bolt member 50 in nonrotating relation relative to fastening portion 36, and likewise locks second washer member 60 in nonrotating condition. Accordingly, nut 62 may be tightened to create any desired degree of frictional engagement with faceshield 20, and any degree of pivoting of faceshield 20 thereafter will not alter the degree of tension thereon. Such a fastening system thus avoids the problem commonly encountered in which repeated pivoting tends to loosen the frictional engagement between members.

According to the present invention there is provided a convenient solid stop member to assure that faceshield 20 does not pivot downwardly further than desired, e.g., in response to downwardly directed impact, and thereby potentially injure the wearer. Extending pin 58 of first washer member 56 extends a distance through circular hole 44, 46 or 48 and into the plane of faceshield 20. An inverted V-shaped groove 29 in faceshield 20 is oriented to centrally engage pin 58 when faceshield 20 is in it fully down, protective orientation, thereby preventing faceshield 20 from continuing beyond such position and assuring additional safety to the wearer.

As can now be appreciated, proper alignment between pin 58 and groove 29 of faceshield 20 is conveniently maintained independent of whether bolt member 50 is positioned in hole 38, 40 or 42, because pin 58 moves correspondingly with bolt member 50. In addition, and more significantly, the position of faceshield 20 relative to the front edge of its helmet is conveniently adjustable to assure a proper sealing relationship therebetween, such that faceshield assembly 10 may be safely utilized with a wide range of helmets of different designs and sizes. Additionally, faceshield 20 may be conveniently locked in its protective orientation by the simple expedient of turning nut 62 to a substantial tightness, so that an impact or opponent's urging would not pivot the faceshield and endanger the wearer.

As shown in FIG. 1, holes 38, 40 and 42 may be oriented for small, medium and large sizes of a particular helmet design. Alternatively, bolt member 50 could be conveniently fixed in position along a continuum of positions in fastening portion 36 without departing from the purposes of the invention.

With reference to FIGS. 1, 2 and 4, an auxiliary front strap 90 may also be conveniently attached to frontal portions of brackets 30 and 70 and positioned across the front, upraised portion of the helmet 12 in order to provide additional security to faceshield assembly 10 in the event of a rearward-directed impact. As shown in FIG. 3, front strap 90 will generally not be needed, particularly where the curved design of the helmet edge provides a fixed place of rest for front arm 32.

Of course the invention is not intended to be limited by the description of preferred embodiments thereof, and reference should be made to the claims which follow.

I claim:

1. A riot faceshield assembly adapted for use with a variety of protective helmets of varying sizes, comprising:
    a transparent protective faceshield member for protecting the face of a user;
    first and second bracket members, each of said bracket members including intermediate faceshield member fastening means for pivotally securing said faceshield member for movement between a protective orientation and an upraised position, each of said bracket members further including front and rear helmet engaging arms for engaging the edge of said helmet at positions in front of and behind the position of said intermediate faceshield member fastening means to limit the upward movement of said faceshield assembly relative to said helmet;
    said intermediate faceshield member fastening means including at least two distinct pivot points to which said faceshield member may be pivotally secured, to permit said faceshield member to be adjusted in position relative to said front edge of said helmet to maintain said generally sealing relationship with helmets of different dimensions;
    strap means secured at one end adjacent one of said bracket members and at its other end adjacent the other of said bracket members and adapted to be positioned over the top of said helmet to provide an upward bias upon said bracket members to urge said engaging arms against said edge of said helmet;
    further wherein said bracket members are configured relative to said helmet to bring said faceshield member into a generally sealing relationship with the front edge of said helmet when said faceshield member is pivoted into its protective orientation; and
    means for preventing said faceshield member from pivoting beyond said protective orientation, wherein said preventing means includes a solid pin member secured within each of said bracket members and positioned to rest in groove means in said faceshield member when said faceshield member is pivoted into said protective orientation, said pin members being movable to different positions relative to said bracket members to correspond to movement of said faceshield member between said at least two distinct pivot points.

2. The faceshield assembly as set forth in claim 1 wherein each of said intermediate faceshield member fastening means comprises:
    a threaded bolt member extending through said bracket member and said faceshield member, said bolt member secured to be nonrotatable when extending through said bracket member;
    first washer means positionable between said bracket member and the head of said bolt member, said first washer means secured to be nonrotatable relative to said bracket member when so positioned;
    a rotatable threaded nut member threadingly engageable to the portion of said bolt member extending through said bracket member and said faceshield member; and
    second washer means positionable between said nut member and said bracket member and faceshield member, said second washer means secured to be nonrotatable relative to said bolt member when so positioned;
    whereby said nut member is loosenable on said bolt member to permit said faceshield member to pivot relative to said bracket member and tightenable on said bolt member to securely fix the position of said faceshield member into said protective orientation, wherein the relative nonrotatable fixation of said first and second washer means and said bolt member permits said faceshield member to be pivoted without affecting the degree of tightness of said nut member on said bolt member.

3. The faceshield assembly as set forth in claim 2 further comprising means for preventing said faceshield member from pivoting beyond said protective orientation, wherein said preventing means includes a solid pin member fixed on each of said first washer means and extending through an orifice in a respective bracket member to fix said first washer means to said bracket member, said pin member extending beyond said bracket member in a position to rest in groove means in said faceshield member when said faceshield member is pivoted into said protective orientation to prevent said faceshield member from pivoting therebeyond.

4. The faceshield assembly as set forth in claim 1, further comprising:
    means for adjusting the length of said strap means to adapt said faceshield assembly for use with helmets of different dimensions.

5. The faceshield assembly as set forth in claim 4, wherein said strap means is non-stretchable in its elongated dimension to prevent said faceshield assembly from being jarred from a helmet to which it is attached.

6. The faceshield assembly as set forth in claim 5, further comprising:

a front strap member secured at each of its ends to portions of said bracket members adjacent said front engaging arms, and positionable across frontal portions of a helmet to which said faceshield assembly is attached to prevent said faceshield assembly from being jarred toward the rear of said helmet by frontal impacts to said faceshield assembly.

7. The faceshield assembly as set forth in claim 1 wherein said front and rear helmet engaging arms of each of said bracket members are spaced apart a distance at least one third of the distance from the front edge to the rear edge of said helmet.

8. The faceshield assembly as set forth in claim 1, further comprising:

resilient sealing means mounted to said faceshield member in a position to sealingly engage the front edge of said helmet when said faceshield member is pivoted into said protective orientation.

* * * * *